US008431741B2

(12) United States Patent
Veghini et al.

(10) Patent No.: US 8,431,741 B2
(45) Date of Patent: Apr. 30, 2013

(54) PROCESS FOR THE HYDROGENATION OF KETOESTERS

(75) Inventors: Dario Veghini, Wohlen (CH); Markus Bicker, Visp (CH); Miguel Angel Caraucán Dávila, Birgisch (CH); Golo Heckmann, Ingelheim (DE); Thomas Ward, St-Blaise (CH); Christophe Malan, Peseux (CH); Julien Pierron, Neuchâtel (CH); Antonio Zanotti-Gerosa, Cambridge (GB); Hans Nedden, Sawston (GB); Laleh Jafarpour, Milford, MA (US)

(73) Assignee: Lonza Ltd, Basel (CH)

( * ) Notice: Subject to any disclaimer, the term of this patent is extended or adjusted under 35 U.S.C. 154(b) by 0 days.

(21) Appl. No.: 13/104,114

(22) Filed: May 10, 2011
(Under 37 CFR 1.47)

(65) Prior Publication Data
US 2012/0016153 A1    Jan. 19, 2012

Related U.S. Application Data

(60) Provisional application No. 61/333,462, filed on May 11, 2010.

(30) Foreign Application Priority Data

May 11, 2010   (EP) .................................... 10004966

(51) Int. Cl.
*C07C 229/00*   (2006.01)
(52) U.S. Cl.
USPC .......................................... 562/579; 562/567
(58) Field of Classification Search .................... None
See application file for complete search history.

(56) References Cited

U.S. PATENT DOCUMENTS

| | | | |
|---|---|---|---|
| 6,939,981 B1 * | 9/2005 | Boaz | 556/14 |
| 7,057,064 B2 * | 6/2006 | Proctor et al. | 560/179 |
| 2007/0078279 A1 * | 4/2007 | Mettler | 560/184 |

FOREIGN PATENT DOCUMENTS

| | | |
|---|---|---|
| EP | 0 295 109 A1 | 12/1988 |
| EP | 0295109 * | 12/1988 |
| EP | 0 366 390 A2 | 5/1990 |
| EP | 0 399 764 A1 | 11/1990 |
| WO | WO 00/29370 A1 | 5/2000 |
| WO | WO 03/097569 A1 | 11/2003 |
| WO | WO 2005/049545 A1 | 6/2005 |

OTHER PUBLICATIONS

Pavlov et al., Russian Chemical Buletin, vol. 49, No. 4, Apr. 2000, pp. 728-731.*

(Continued)

*Primary Examiner* — Karl J Puttlitz
(74) *Attorney, Agent, or Firm* — Hoffmann & Baron, LLP

(57)   ABSTRACT

The invention relaters to a process for the production of an (S)- or (R)-4-halo-3-hydroxybutyrate, comprising reacting a 4-haloacetoacetate with hydrogen in the presence of
a solvent, the solvent being a solvent mixture, which comprises a first solvent and a second solvent, wherein the first solvent is an aliphatic alcohol, preferably methanol, ethanol or propanol, and the second solvent is aprotic and comprises at least one oxygen atom; and
a catalyst of the formula [RuXYZ]X, wherein
X is halogen, preferably Cl or Br, or OAc, acetoacetate, allyl or $ClO_4$,
Y is a bidentate organic ligand having two phosphine groups, and
Z is an arene, preferably cymene, benzene, xylene or toluene, or a polyene, preferably a diene, or an alkene.

29 Claims, 4 Drawing Sheets

OTHER PUBLICATIONS

V.A. Pavlov, E.V. Starodubtseva, M.G. Vinogradov, V.A. Ferapontov, O.R. Malyshev and L. Heise "Enantioselective hydrogenation of β-keto esters catalyzed by chiral binaphtylbisphosphine ruthenium complexes" Russian Chemical Bulletin, vol. 49, No. 4, Apr. 2000, 728-731—© 2000 Kluwer Academic/Plenum Publishers.

Wenjun Tang and Xuma Zhang "New Chiral Phosphorus Ligands for Enantioselective Hydrogenation" Chem. Rev 2003, 103, 3029-3069—© 2003 American Chemical Society—Published on Web Jun. 6, 2003.

Xiaobing Wan, Yanhui Sun, Yunfei Luo, Dao Li, and Zhaoguo Zhang "Synthesis of Bulky and Electron-Rich Derivative of SEGPHos and Its Application in Ru-Catalyzed Enantioselective Hydrogenatiom of β-Ketoesters" J. Org. Chem. 2005, 70, 1070-1072—© 2005 American Chemical Society—Published on Web Jan. 5, 2005.

G. Winkhaus and H. Singer "Ruthen(II)-komplexe mit zweizähnigem cycloheptatrien and benzol" Journal of Organometallic Chemistry, vol. 7, Issue 3, Mar. 1967, pp. 487-491—© 1967 Published by Elsevier Science B.V. All rights reserved—Abstract in English.

R.A. Zelonka and M.C. Baird "Benzene Complexes of Ruthenium (II)" Canadian Journal of Chemistry, vol. 50, 1972, 3063-3072.

The Journal of Organic Chemistry, vol. 41, 1976, JOCEAH 41 (18-26) 2943-4178 (1976), ISSN 0022-3263—September-December, Author Index.

\* cited by examiner

Figure 2

Table 1:

| Exp. | Catalyst | S/C | Conc. S | Solvent | Temp. [°C] | Press. [bar] | Time [hrs] | Conv. [%] | ee [%] | Config |
|---|---|---|---|---|---|---|---|---|---|---|
| 3 | (R)-Me-BoPhoz-RuCl$_2$(DMF)$_2$ | 20000 | 3 M | EtOH/THF | 85 | 25 | 5 | 20 | n.a | |
| 4 | (S)-H$_8$-BINAM-P-RuCl$_2$(DMF)$_2$ | 20000 | 3 M | EtOH/THF | 85 | 25 | 5 | 19 | n.a | |
| 5 | [(S)-BINAP-Ru(p-cymene)Cl]Cl | 75000 | 3 M | EtOH/THF | 100 | 25 | 3 | 100 | 96 | R |
| 6 | [(R)Xyl-P-Phos-Ru(benzene)Cl]Cl | 75000 | 3 M | EtOH/THF | 100 | 25 | 3 | 100 | 95 | S |
| 7 | [(R)Xyl-P-Phos-Ru(benzene)Cl]Cl | 150000 | 3 M | EtOH/THF | 100 | 25 | 6 | 99 | 96 | S |
| 8 | [(R)P-Phos-Ru(benzene)Cl]Cl | 40000 | 3 M | EtOH/THF | 100 | 25 | 2,75 | 100 | 98 | S |
| 9 | [(S)Xyl-P-Phos-Ru(benzene)Cl]Cl | 20000 | 3 M | EtOH/THF | 100 | 25 | 2 | 100 | 98 | R |
| 10 | [(S)Xyl-P-Phos-Ru(benzene)Cl]Cl | 20000 | 4 M | EtOH/THF | 100 | 25 | 2,25 | 100 | 96 | R |
| 11 | [RuCl(p-cymeme)((S)-Segphos)]Cl | 35000 | 3 M | EtOH/THF | 100 | 15 | 2,7 | >90 | 97,66 | R |
| 12 | (S)-(−) BINAP Cl (cymene)RuCl | 70000 | 3 M | EtOH/THF | 100 | 40 | 2,37 | 100 | 96,21 | R |
| 13 | (R)-Tetra-Me-bitiop [RuCl$_2$(p.-Cymol)Cl]$_2$ | 70000 | 50 wt% | EtOH/THF | 100 | 40 | 1,3 | 100 | 96,94 | R |
| 14 | Ru-(S)-C3-Tunephos | 70000 | 3 M | EtOH/THF | 100 | 40 | 3,28 | 100 | 97,89 | R |
| 15 | [(S)-Xyl-P-PhosRuCl (benzene)]Cl | 70000 | 3 M | EtOH/THF | 100 | 40 | 4,54 | 100 | 95,52 | R |
| 16 | Ru-MeO-BIPHEP | 70000 | 3 M | EtOH/THF | 100 | 40 | 3,21 | 100 | 96,48 | R |
| 17 | (S)-(−) BINAP Cl (cymene)RuCl | 70000 | 3 M | EtOH/THF | 100 | 15 | 5,5 | 97,5 | 95,6 | R |

Figur 3

Table 2:

| Exp. | Catalyst | S/C | Conc. S | Solvent | Temp. [°C] | Press. [bar] | Time | ee [%] | Config |
|---|---|---|---|---|---|---|---|---|---|
| 18 Comp. | (S)-(−) BINAP Cl (cymene)RuCl | 70000 | 50%(w/w) | EtOH | 100 | 40 | 4h | 87,98 | R |
| 19 | (S)-(−) BINAP Cl (cymene)RuCl | 70000 | 50%(w/w) | EtOH/Aceton | 100 | 40 | 1h 40min | 94,94 | R |
| 20 | (S)-(−) BINAP Cl (cymene)RuCl | 70000 | 50%(w/w) | EtOH/THF | 100 | 40 | 2h 24min | 96,13 | R |
| 21 Comp. | (S)-(−) BINAP Cl (cymene)RuCl | 70000 | 50%(w/w) | EtOH/Toluol | 100 | 40 | 2h 42min | 92,29 | R |
| 22 Comp. | (S)-(−) BINAP Cl (cymene)RuCl | 70000 | 50%(w/w) | EtOH/CH$_2$Cl$_2$ | 100 | 40 | 4h 19min | 90,95 | R |

Table 3:

| Exp. | Catalyst | S/C | Conc. S [M] | Solvent | Temp. [°C] | Press. [bar] | Time [hrs] | Conv. [%] | ee [%] | Config. |
|---|---|---|---|---|---|---|---|---|---|---|
| 23 | (S)-C3-tunephos[RuCl$_2$(benzene)]$_2$ | 2000 | 1,8 | EtOH/THF | 60 | 50 | 2 | 5,2 | 54,4 | R |
| 24 | [RuCl(p-cymene)(R)-C3-Tunephos]Cl | 35000 | 3 | EtOH/THF | 100 | 15 | 5 | 60 | 96,88 | S |
| 25 | (S)-Tol-binap[RuCl$_2$(benzene)]$_2$ | 2000 | 1,8 | EtOH/THF | 60 | 50 | 2 | 22,6 | 88 | R |
| 26 | [RuCl(p-cymeme)((S)-Binap)]Cl | 35000 | 3 | EtOH/THF | 100 | 15 | 3,1 | >90 | 96,46 | R |
| 27 | (R)-Tetra-Me-bitiop[RuCl$_2$(benzene)]$_2$ | 2000 | 1,8 | EtOH/THF | 60 | 50 | 2 | 95,2 | 96,4 | R |

Figure 4
a) SEGPHOS
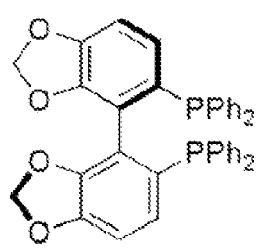
b) Cn-TunePhos
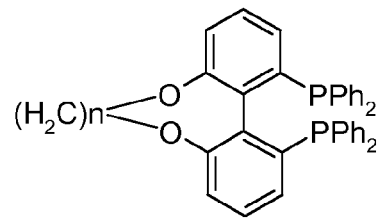
Cn-TUNEPHOS
n = 1, 2, 4, 5, 6
c) P-Phos
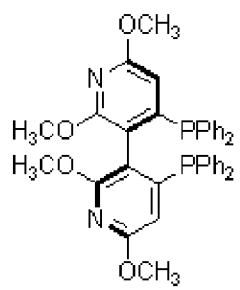
d) MeO-BIPHEP
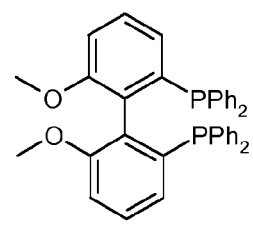
e) tetraMe-BITIOP
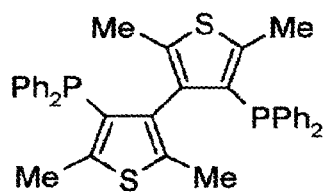
f) BINAP
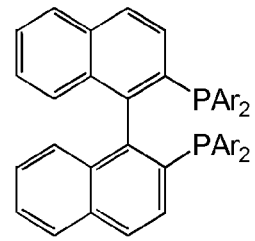
Ar = Ph, *m*-Xyl, *p*-Tol

PROCESS FOR THE HYDROGENATION OF KETOESTERS

CROSS-REFERENCE TO RELATED APPLICATION

This application claims the benefit of priority from U.S. Provisional Patent Application No. 61/333,462 filed May 11, 2010, and European Patent Application bearing Serial Number 10004966.7 filed May 11, 2010, the disclosures of which are incorporated herein by reference.

The invention relates to a process for the production of (S)- or (R)-4-halo-3-hydroxybutyrates from 4-haloacetoacetates. The invention also relates to the production of L-carnitine.

BACKGROUND OF THE INVENTION

The enantioselective hydrogenation of β-ketoesters is an important industrial process for the production of optically active 3-hydroxyesters by means of organic synthesis. The optically active 3-hydroxyesters are important intermediates for producing pharmaceuticals, vitamins or natural products. For example, L-carnitine is produced by amination of ethyl-4-chloro-3-hydroxybutyrate, which can be obtained by hydrogenation of the respective β-ketoester.

Carnitine (vitamin Bt; 3-hydroxy-4-trimethylammoniobutanoate) is a quaternary ammonium compound biosynthesized from the amino acids lysine and methionine. In living cells, it is required for the transport of fatty acids from the cytosol into the mitochondria during the breakdown of lipids for the generation of metabolic energy. It is used as a nutritional supplement. Carnitine exists in two stereoisomers. The biologically active form is L-carnitine, whilst its enantiomer, D-carnitine, is biologically inactive.

When producing L-carnitine in an industrial process, it is desirable to produce the biologically active L-form in high purity.

Various methods have been described in the art for converting β-ketoesters to β-hydroxyesters. In many processes, β-ketoesters are hydrogenated in the presence of an optically active ruthenium catalyst. In these catalysts, a central ruthenium ion is bound in a chelate complex.

For example, WO 2005/049545 discloses methods for preparing enantiomerically pure (S)- or (R)-4-halo-3-hydroxybutyrate in the presence of a ruthenium chelate complex, which comprises a bidentate ligand having two phosphorous binding sites. The chiral ligand is referred to as "Fluoxphos" and comprises four fluorine atoms.

Further catalysts and methods for producing optically active alcohols from β-ketoacid esters are disclosed in EP 0 295 109 A1. The inventors suggest the use of ruthenium catalysts with BINAP and derivatives thereof. In examples 1-17, various substrates are hydrogenated in the presence of such catalysts. However, satisfactory total yields and optical yields of optically active alcohols are only obtainable for some specific reactions.

Other ruthenium-based chiral catalysts for converting β-ketoesters into 3-hydroxyesters are disclosed in EP 0 366 390 A2. In the examples, the hydrogenation of methyl-3-hydroxybutyrate with a large variety of catalysts is studied. However, the total yield and optical yield of the desired product are only sufficient for a limited number of catalysts. For most catalysts, the yields are below 90%, which is not satisfactory for a large-scale industrial production.

Pavlov et al. (Russ. Chem. Bull., 2000, 49, p728-731) studied the efficiency of the enantioselective hydrogenation of β-ketoesters in the presence of BINAP ruthenium complexes. They found that process conditions, such as solvent, pressure and temperature, but also specific combinations of substrate and catalyst have an impact on the total yield and enantiomeric yield. The reactions carried out according to Pavlov et al. require relatively high amounts of catalysts and solvents and high pressure, whereas the yields are often not sufficient.

Thus, processes known in the art often do not provide sufficient yield. However, for an efficient industrial production, it is important to achieve a high total yield as well as a high optical yield. This problem is discussed in WO 03/097569 A1 (para. bridging pages 2 and 3). The inventors conclude that the prior art does not provide methods, which are practical on a commercial scale. Further, the prior art would require low substrate to catalyst ratios to achieve a good enantioselectivity. Since chiral ligands, such as BINAP or other bisarylbiphosphine-based ligand catalysts are expensive, processes requiring low substrate-to-catalyst-ratios are generally uneconomic.

Therefore, the authors suggest a specific continuous process, which should overcome the problems of prior art processes. When converting ethyl-4-chloroacetoacetate into ethyl-4-chloro-3-hydroxybutyrate by the continuous process, relatively high yields and optical yields were obtained whilst using relatively low concentration of catalysts (example 3, figure). However, these advantages are only achieved by carrying out the reaction in a relatively complicated continuous process. The hydrogenation reactor requires high pressure (between 90 and 100 bar) and exact process control. In order to maintain the continuous process conditions, dedicated equipment such as high pressure pumps and devices for supplying, removing and separating the components are necessary. Further, such metal catalysts in solution are highly sensitive against "poisoning" by traces of oxygen. Therefore, the catalyst can become inactivated during storage, leakage of the equipment or when components are not degassed sufficiently. As a result, the yield and selectivity are reduced.

Problem Underlying the Invention

The problem underlying the invention is to provide a method for producing (S)- or (R)-4-halo-3-hydroxybutyrates from 4-haloacetoacetates by hydrogenation, which overcomes the above-mentioned problems.

The process should be applicable for producing highly pure (S)- or (R)-4-halo-3-hydroxybutyrate. The enantiomeric purity and the total yield shall be high.

The process shall be carried out in a simple manner. The number of process steps shall be relatively low and the process shall not require complicated apparatuses. Overall, the process shall be cost- and labour-efficient.

Specifically, the process shall be so efficient that it can be carried out in a batch process. The process shall be applicable with standard equipment for reactions under pressure, without stringent process control and without complicated equipment. It shall not be necessary to carry out the reaction in a continuous process, for example as disclosed in WO 03/097569.

Further, the process shall only require low amounts of the necessary compounds, such as solvent and catalyst. As little solvent and catalyst as possible shall be used, whereas the substrate concentration of β-ketoester and the ratio substrate/catalyst shall be high. The use of additional compounds, especially acids or bases, shall be avoided.

Moreover, the process shall be energy-efficient and applicable under relatively mild conditions. Specifically, the use of high pressure and temperature for extended reaction times shall be avoided.

Specifically, the inventive process shall be applicable for producing L-carnitine precursors, especially (R)-ethyl-4-chloro-3-hydroxybutyrate. The invention shall also provide a simple and efficient process for the production of L-carnitine.

DISCLOSURE OF THE INVENTION

Surprisingly, the problem underlying the invention is solved by the process according to the claims. Further inventive embodiments are disclosed throughout the description.

Subject of the invention is a process for the production of an (S)- or (R)-4-halo-3-hydroxybutyrate, comprising reacting a 4-haloacetoacetate with hydrogen in the presence of a solvent, the solvent being a solvent mixture, which comprises a first solvent and a second solvent, wherein the first solvent is an aliphatic alcohol and the second solvent is aprotic and comprises at least one oxygen atom; and a catalyst of the formula [RuXYZ]X, wherein
  X is halogen, preferably Cl or Br, or OAc, acetoacetate, allyl or ClO$_4$,
  Y is a bidentate organic ligand having two phosphine groups, and
  Z is an arene, preferably cymene, benzene, xylene or toluene, or a polyene, preferably a diene, or an alkene.

The catalyst is a ruthenium catalyst. Further, it is an asymmetric catalyst.

The two residues X can either be identical or different from each other. It is preferred that both residues X are Cl.

In principle, Z may be any coordinating ligand, which comprises at least one double bond. Preferably, Z comprises 4 to 30, more preferably 5 to 15 carbon atoms.

Preferably, Z is arene. Preferably, the arene is substituted or unsubstituted benzene. Preferably, the benzene is substituted with one or more groups selected from a C1-4 alkyl group, a C1-4 alkoxy group, a carboalkoxy group or a halogen atom. In preferred embodiments, Ar is benzene, cymene (p-cymene, 4-isopropyltoluene), toluene, xylene, trimethylbenzene, hexamethylbenzene, ethylbenzene, t-butylbenzene, cumene (isopropylbenzene), methyl benzoate, methyl(methylbenzoate), methyl(chlorobenzoate), anisole, methylanisole, chlorobenzene, dichlorobenzene, trichlorobenzene, bromobenzene or fluorobenzene. It is highly preferred that Ar is cymene, toluene, xylene or benzene.

Z may also be a polyene or an alkene, preferably a cyclic polyene or arene. For example, the polyene may be butadiene or cyclooctadiene. The alkene may be cyclooctene.

The ligand Y is an organophosphorus ligand. The two phosphine groups of a ligand molecule coordinate the central ruthenium atom. Each phosphine group comprises one phosphorus atom having three organic substituents. One of the substituents represents the linking (bridging) element to the second phosphine group. This bridging substituent preferably comprises a structural element, in which two aromatic rings, preferably identical rings, are attached directly to each other via a single bond, thereby forming a biaryl group. Preferably, the biaryl group is a biphenyl, bipyridine or bithiophene group. Preferably, the other two substituents of each phosphorus are aryl, araryl and/or alkyl substituents.

It is preferred that the ligand Y is C2-symmetric. Preferably, the ligand Y does not comprise a nitrogen atom directly attached to a phosphorus atom.

In a preferred embodiment of the invention, Y has the formula X$_2$P—Z—PX$_2$, wherein
  Z comprises at least one aromatic hydrocarbon,
  the residues X are selected independently from each other, and
  at least one residue X is an aryl or araryl group.

Preferably, X is aryl or araryl, preferably phenyl or substituted phenyl, preferably phenyl substituted with alkyl, more preferably tolyl or xylyl. Preferably, all four X are aryl or araryl. Preferably, all X are identical. Z preferably comprises a biaryl group as outlined above. Preferably, each X has between 1 and 15 carbon atoms, or between 5 and 10 carbon atoms.

In a more preferred embodiment, Y has the formula (I)

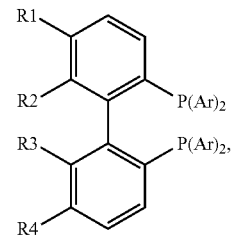

wherein
  Ar is aryl or araryl, preferably phenyl or phenyl substituted with alkyl side chains having 1 to 10 carbon atoms, preferably phenyl, tolyl or xylyl, wherein all Ar are selected independently from each other, but preferably are identical, and R1, R2, R3 and R4 are selected independently from each other, and are preferably selected from H, OH, halogen and organic side chains having 1 to 10 C-atoms, preferably 1 to 4 carbon atoms, which are preferably alkoxy or alkyl, preferably methyl, ethyl, methoxy, ethoxy, or a cyclic alkoxy group bridging residue R1 with R2 and/or residue R3 with R4 and/or residue R2 with R3. The cyclic alkoxy group preferably comprising 2, 3, 4 or 5 carbon atoms (as the Cn moiety of Cn TUNEPHOS, FIG. 4 b)).

Alternatively, Y may be a derivative of a compound of formula (I), in which at least one phenyl ring, preferably both biphenyl rings, are substituted each by a heterocyclic aromatic ring, preferably by a ring comprising one heteroatom, which is preferably nitrogen or sulphur. Preferably, the heterocyclic derivative comprises a bipyrdine or bithiophene structure instead of a bipyridine structure. In this embodiment, the residues R1, R2, R3 and R4 may be at positions of the aromatic rings, which are different from those in formula (I), and preferably at the α-positions next to the heteroatoms (as in P-Phos or BITIOP, see FIG. 4 c(, e)).

Preferably, Y is selected from BINAP, SEGPHOS, TunePhos, P-Phos, BITIOP, BIPHEP, and derivatives thereof. The derivatives are those, which have the molecular structure of the catalyst, but with at least one additional substituent attached to at least one aromatic ring. Preferably, the additional substituent is alkyl, alkoxy or halogen.

Preferably, the catalyst is selected from [RuCl(p-cymene)((S)-BINAP)]Cl, [RuCl(p-cymene)((R)-BINAP)]Cl, [(R)Xyl-P-Phos-Ru(benzene)Cl]Cl, [(R)P-Phos-Ru(benzene)Cl]Cl, [(S)P-Phos-Ru(benzene)Cl]Cl, [(S)Xyl-P-Phos-Ru(benzene)Cl]Cl, [(S)P-Phos-Ru(benzene)Cl]Cl, [RuCl(p-cymene)((S)-SEGPHOS)]Cl, [RuCl(p-cymene)((R)-SEGPHOS)]Cl, (R)-tetra-Me-BITIOP[RuCl$_2$(p-cymol)]$_2$, [(S)-C3-TunePhos-Ru(p-cymene)Cl]Cl, [RuCl(p-cymene)

(R)-C3-Tunephos]Cl, (S)-Tetra-Me-BITIOP [RuCl$_2$(p-Cymol)]$_2$, [(S)-MeO-BIPHEP-Ru(pcymene)Cl]Cl and [(R)-MeO-BIPHEP-Ru(pcymene)Cl]Cl.

Further preferred BINAP catalysts are [RuCl(p-cymene)((R)-toIBINAP)]Cl, [RuCl(p-cymene)((R)-xylBINAP)]Cl [RuCl(p-cymene)((S)-toIBINAP)]Cl, [RuCl(p-cymene)((S)-xylBINAP)]Cl, [(S)-BINAP-Ru(benzene)Cl]Cl, [(R)-BINAP-Ru(benzene)Cl]Cl, [RuCl(benzene)((R)-toIBINAP)]Cl, [RuCl(benzene)((R)-xylBINAP)]Cl [RuCl(benzene)((S)-toIBINAP)]Cl and [RuCl(benzene)((S)-xylBINAP)]Cl.

Further preferred SEGPHOS catalysts are [RuCl(benzene)((S)-SEGPHOS)]Cl, [RuCl(benzene)((R)-SEGPHOS)]Cl, [RuCl(p-cymene)((S)-xyl-SEGPHOS)]Cl, [RuCl(p-cymene)((R)-xyl-SEGPHOS)]Cl, [RuCl(benzene)((S)-xyl-SEGPHOS)]Cl and [RuCl(benzene)((R)-xyl-SEGPHOS)]Cl.

Further preferred P-Phos catalysts are [(S)Xyl-P-Phos-Ru(cymene)Cl]Cl, [(R)Xyl-P-Phos-Ru(cymene)Cl]Cl [(R)P-Phos-Ru(cymene)Cl]Cl and [(S)P-Phos-Ru(cymene)Cl]Cl.

Further preferred TunePhos catalysts are [RuCl(benzene)(S)-C3-Tunephos]Cl, [RuCl(benzene)(R)-C3-Tunephos]Cl, [RuCl(p-cymene)(S)-C1-Tunephos]Cl, [RuCl(p-cymene)(R)-C1-TunePhos]Cl, [RuCl(benzene)(S)-C1-TunePhos]Cl, [RuCl(benzene)(R)-C1-TunePhos]Cl, [RuCl(p-cymene)(S)-C5-TunePhos]Cl, [RuCl(p-cymene)(R)-C5-TunePhos]Cl, [RuCl(benzene)(S)-C5-TunePhos]Cl and [RuCl(benzene)(R)-C5-TunePhos]Cl.

Further preferred BITIOP catalysts are (R)-Tetra-Me-BITIOP [RuCl$_2$(benzene)]$_2$ and (R)-Tetra-Me-BITIOP [RuCl$_2$(p-benzenel)]$_2$.

Further preferred BIPHEP catalysts are [(R)-MeO-BIPHEP-Ru(benzene)Cl]Cl, [(S)-MeO-BIPHEP-Ru(benzene)Cl]Cl, [(R)-Cl-MeO-BIPHEP-Ru(benzene)Cl]Cl, [(S)-Cl-MeO-BIPHEP-Ru(benzene)Cl]Cl, [(R)-Cl-MeO-BIPHEP-Ru(cymene)Cl]Cl and [(S)-Cl-MeO-BIPHEP-Ru(cymene)Cl]Cl.

In a preferred embodiment of the invention, the process for the production of an (S)- or (R)-4-halo-3-hydroxybutyrate comprises reacting a 4-haloacetoacetate in the presence of a solvent with hydrogen in the presence of a catalyst of the formula [RuXArY]X, wherein X is halogen, preferably Cl, or OAc, allyl or ClO$_4$, Y is BINAP, or a derivative of BINAP having at least one aromatic ring substituted with an alkyl group, Ar is an arene, preferably cymene, benzene, xylene or toluene.

According to the invention, it is preferred that Y is BINAP. BINAP is an abbreviation for the organophosphorus compound 2,2'-bis(diphenylphosphino)-1,1'-binaphthyl (CAS number of (S)-form: 76189-56-5). BINAP is a chiral ligand, which is used in asymmetric synthesis. It consists of a pair of 2-diphenylphosphinonaphthyl groups linked at the 1 and 1' positions. In formula (I) below, BINAP is the compound in which all R are H.

The derivatives of BINAP are those which have the molecular structure of BINAP, but with at least one alkyl group attached to at least one aromatic ring. The derivative Y of BINAP is preferably one of formula (I):

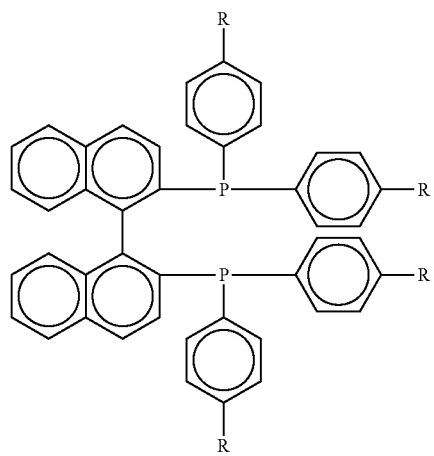

wherein R is preferably selected from H and C1-C4 alkyl, preferably methyl or ethyl. The residues R can be identical or different from each other in one molecule. Some specific BINAP ligands are shown in FIG. 4 f).

Bidentate phosphine ligands, which can be used according to the invention, are known in the art. For example, a summary of catalysts and ligands and their applications is provided in Tang and Zhang, 2003, Chem. Rev. 2003, 103, 3029-3069.

SEGPHOS (CAS Nrs. 244261-66-3 (R-isomer); 210169-54-3 (S)-isomer) is a known ligand for asymmetric synthesis, which comprises a biphenyl structure as shown in FIG. 4 a).

TunePhos is another known ligand, which comprises a biphenyl structure as shown in FIG. 4 b). Various forms of TunePhos are available with varying chain length of the cyclic aliphatic ether group. For example, (S)-C3-TunePhos (CAS Nr. 486429-99-6) comprises a cyclic aliphatic group having three carbon atoms.

P-Phos (CAS Nr. 221012-82-4 (R)-isomer) is another known ligand shown in FIG. 4 c), which comprises a bipyridine structure. Derivatives are known in the art and commercially available, for example those in which methyl groups are attached to the phenyl rings.

BITIOP is another known ligand available from Austin Chemical Corp., US. It comprises a bithiophene structure, which may be substituted as in TetraMe-BITIOP (FIG. 4 e)).

BIPHEP (CAS-Nr. 133545-16-1(R)-isomer) is also known in the art and shown in FIG. 4 d). Derivatives are known having additional substituents attached to the biphenyl group, such as additional chlorines.

The catalyst or ligand, specifically BINAP or a derivative thereof, can be the (R)- or (S)-enantiomer. The enantiomeric form is chosen depending on the desired product.

In a highly preferred embodiment of the invention, the catalyst is [RuCl(p-cymene)((S)-BINAP)]Cl. It was found that the inventive reaction is highly effective when using this specific catalyst.

A wide range of ligands X, Y and Z and catalysts [RuXYZ]X, specifically [RuXArY]X, is commercially available, for example from Sigma-Aldrich, US, Strem Chemicals, US, or Takasago, Japan. Specific catalysts can also be prepared by known methods, for example those disclosed in EP 0 366 390 A2. For example, the compound wherein X is Cl of the formula [RuCl(Ar)(BINAP)]Cl can be quantitatively synthesized by reacting the metal precursor [RuCl$_2$(Ar)]$_2$ with a ligand BINAP in a solvent, e.g., methanol, ethanol, benzene or methylene chloride or a mixture thereof, at a temperature of from 25° C. to 50° C. for a period of from 30 minutes to 3 hours and removing the solvent from the reaction mixture by distillation under reduced pressure. In an alternative pathway, the catalyst can be prepared in situ by mixing the metal precurser with the corresponding ligand, for example as disclosed by Zhang, J. Org. Chem. 2005, 70, 1070-1072. The starting compound [RuCl$_2$(Ar)]$_2$ is commercially available, or can be prepared by the processes disclosed in G. Wikhaus, J. Org. Chem., Vol. 7, p. 487 (1976) or R. A. Zelonka, Can. J. Chem., Vol. 50, p. 3643 (1972) Other catalysts can be prepared when using other bidentate ligands instead of BINAP.

Preferred BINAP catalysts are also [RuCl(p-cymene)(BINAP)]Cl, [RuCl(p-cymene)(tol-BINAP)]Cl, [RuCl(p-cymene)(xyl-BINAP)]Cl, [RuCl(p-cymene)((H8-BINAP)]Cl, [RuI(p-cymene) (MeO-BINAP)], [RuI(p-cymene)(p-tol-BINAP)]I, [RuI(p-cymene)(m-tol-BINAP)]I, [RuI(p-cymene)(p-Cl-BINAP)]I, [RuI(p-cymene)(p-F-BINAP)]I, [RuI(p-cymene)(3,5-DiMet-BINAP)]I and [RuI(p-cymene) (H8-BINAP)]I. All catalysts can be used either with (S)- or (R)-BINAP, depending on the respective desired product.

The inventive reaction is for converting 4-haloacetoacetate into the desired (S)- or (R)-4-halo-3-hydroxybutyrate. Although the esters can be derived from any alcohol, it is preferred that they are alkyl esters, specifically a methyl, ethyl, 1-propyl, 2-propyl, 1-butyl, 2-butyl or tert-butyl ester.

The inventive reaction is a hydrogenation reaction, which is carried out in the presence of gaseous hydrogen. In principle, methods for the hydrogenation of β-ketoesters in the presence of ruthenium catalysts are known in the art, for example from EP 0 366 390, EP 0 295 109 or EP 0 339 764 A1. Thus, the processes and process conditions disclosed therein are hereby incorporated by reference. However, the inventive process is highly efficient and thus the selection and amount of substances and the reaction conditions should be adapted as outlined further below.

In a preferred embodiment of the invention, the 4-haloacetoacetate is ethyl-4-chloroacetoacetate and the product is (R)-ethyl-4-chloro-3-hydroxybutyrate. In this embodiment, [(S)-(−)-BINAP-Cl (cymene)Ru]Cl is a preferred catalyst. In this embodiment, the product can be converted to L-carnitine by amination and subsequent hydrolysis, as disclosed for example in EP 1131279.

It was found that when using the specific combination of substrate and catalyst according to the invention, the reaction is highly efficient. It is not necessary to dilute the substrate with high amounts of solvent as in similar reactions described previously. The inventive process only requires relatively low amounts of solvent. In a preferred embodiment of the invention, the concentration of the 4-haloacetoacetate in the solvent is at least 25% (w/w), preferably at least 40% (w/w), more preferably at least 50% (w/w). Preferably, the concentration of the 4-haloacetoacetate in the solvent is between 25% and 75% (w/w), preferably between 35% and 65% (w/w). It was found that a concentration about 45-55% (w/w) is applicable. A part from using less solvent, the low amount of solvent renders the reaction more economical, since the throughput is higher, smaller production plants can be used and less energy for heating is consumed.

Due to the efficiency of the inventive process, only low amounts of catalyst are necessary. The molar ratio 4-haloacetoacetate/catalyst is preferably above 35,000, preferably above 50,000, more preferably above 60,000 or above 70,000. In preferred embodiments, the ratio is between 35,000 and 100,000, preferably between 50,000 and 90,000 or between 60,000 and 80,000. The reduced amount of catalyst compared to processes described previously renders the inventive process significantly cheaper and thus applicable for large industrial-scale production. In preferred embodiment, the catalyst is recycled. The catalyst can then be reused in multiple batch reactions.

In a preferred embodiment of the invention, the process is a batch process. In a batch process, the hydrogenation reaction is not carried out continuously. In contrast, the reaction is carried out in a reactor and is terminated upon conversion of the substrate into the product. Subsequently, the product is removed from the reactor. Batch processes are simpler and more flexible than continuous processes. In a batch process, the product can be produced upon demand. Since a continuous process requires continuous process conditions, the process has to be monitored and strictly controlled. In principle, a batch process is different from a continuous product, because the amounts and concentrations of the reactants change during the progression of the reaction. However, although the present inventive process is efficient as a batch process, it can also be carried out in a continuous process.

In a preferred embodiment of the invention, the reaction mixture does not comprise an additional acid, such as Lewis acids, especially HCl, or additional base, such as amines. According to the invention, it is possible to carry out the reaction without such additives. In a preferred embodiment, only the substrate, the solvent and the catalyst are added to the reaction mixture as the non-gaseous components. Depending on the solvent used, a stabilizer, specifically an anti-oxidant and/or an anti-peroxide, can be added, such as butylhydroxytoluene (BHT). For example, when the solvent comprises THF, it is advantageous to add BHT to inhibit peroxide formation.

In a preferred embodiment of the invention, the 4-haloacetoacetate is an ester of an aliphatic alcohol, preferably one having 1 to 4 carbon atoms. Especially preferred are methyl, ethyl, n-propyl, iso-propyl, n-butyl, iso-butyl and tert-butyl esters. Most preferred are methyl and ethyl esters.

It was found that the inventive reaction is especially effective when using a specific solvent mixture. The solvent mixture comprises a first protic solvent and a second aprotic solvent. Preferably, the solvent mixture consists of said first and second solvent. Preferably, the combined amount of first and second solvent in the total solvent mixture is at least 80% (w/w), more preferably at least 90% (w/w) or 95% (w/w). The solvent mixture is an organic solvent mixture and thus does not, or substantially does not comprise water. However, water may be present in small or trace amounts, for example below 5% (w/w), below 1% (w/w) or below 0.1% (w/w).

The first solvent is an aliphatic alcohol, preferably one having 1 to 4 carbon atoms. Especially preferred are methanol, ethanol, 1-propanol, 2-propanol, 1-butanol, 2-butanol or tert-butanol. In a preferred embodiment of the invention, the first solvent is ethanol or methanol. In general, it is highly advantageous if the first solvent is identical to the alcohol of the ester. For instance, if the substrate is an ethyl ester, it is advantageous to use ethanol as the first solvent, whereas when the substrate is a methyl ester, the first solvent should be methanol. Thereby, the formation of mixed esters is avoided. Preferably, the first solvent is ethanol and the ester is an ethyl ester, or the first solvent is methanol and the ester is a methyl ester.

The second solvent is aprotic and comprises at least one oxygen atom. Aprotic solvents do not act as Bronsted acids in the reaction mixture. Specifically, aprotic solvents do not have a free hydroxy group. The aprotic second solvent is a polar aprotic solvent. In a preferred embodiment of the invention, the second solvent is an ether, preferably a cyclic ether, more preferably tetrahydrofuran. In another preferred embodiment, the second solvent is a ketone, preferably acetone; or an ester, such as methyl acetate or ethyl acetate. The second solvent should be inert in the reaction.

In a highly preferred embodiment of the invention, the first solvent is ethanol, the second solvent is THF and the substrate is an ethyl ester. It was found that the inventive reaction is highly efficient when carried out in a mixture of ethanol/THF. In another highly preferred embodiment of the invention, the first solvent is methanol, the second solvent is THF and the substrate is a methyl ester.

In a preferred embodiment of the invention, the ratio of the first solvent to the second solvent is between 5:1 and 1:5 (w/w), more preferably between 2:1 and 1:2 (w/w) or between 1:1.5 and 1.5:1 (w/w). In a preferred embodiment, the ratio is about 1:1.

In a preferred embodiment of the invention, the reaction is carried out in the presence of hydrogen at a pressure between 5 bar and 200 bar, preferably between 5 bar and 40 bar or between 10 and 50 bar and/or at a temperature between 50° C. and 150° C., preferably between 70° C. and 130° C. Preferably, the reaction is carried out in the presence of hydrogen at a pressure between 10 and 20 bar and/or at a temperature between 90 and 110° C. It was found that the yield might be higher, if the pressure is at least 15 bar or at least 20 bar. Further, it was found that the yield can often be increased when raising the reaction temperature above 60° C. Preferably, the reaction temperature is above 70° C., or above 80 or above 90° C. The reaction temperature may not exceed 200° C. or 150° C. Preferably, the temperature is between 75 and 150° C., more preferably about 100° C.

Preferably, the reaction is carried out in an autoclave or a pressure reactor. The reaction mixture and the reactor should not comprise oxygen or as little oxygen as possible. Thus, the reactor, the reaction mixture and all liquids should be filled and treated with an inert gas prior to the reaction.

For example, the reaction may be carried out for 1 to 10 hours, preferably for 1 to 6 hours, or for 2 to 6 hours, or for 1 to 4.5 hours, preferably under stirring. In a specific embodiment, the reaction time may be between 30 min and 2.5 hours.

After termination of the reaction, the product is isolated from the reaction mixture. In a preferred embodiment of the invention, the solvent is removed from the reaction mixture by distillation. In a preferred embodiment of the invention, the solvent is separated from the reaction mixture by distillation and recycled in the process. It was found that the inventive process is so efficient that only low amounts of undesired low molecular weight side-products are obtained. Thus, it is possible to recycle the solvent, especially the solvent mixture, in the reaction. Preferably, the solvent is reused several times, for example at least 5 or at least 20 times. Usually, the solvent can be removed under vacuum, for example about 100 to 300 mbar, whilst heating the solution for example to about 20 to 60° C.

The solvent can also be removed from the reaction mixture by other known methods, such as pervaporation, nanofiltration, membrane separation, membrane filtration, electrodialysis, diafiltration, reverse osmosis, liquid chromatography (LC), HPLC, extraction, crystallization and the like.

In a preferred embodiment of the invention, after separating the solvent mixture from the reaction solution in a first distillation, the 4-halo-3-hydroxybutyrate is separated in a second distillation. The second distillation can be carried out at approximately 90 to 150° C., preferably 100 to 130° C., depending on the specific product, in a vacuum, for example at 1-5 mbar. The distillations can be carried out in a batch process or a continuous process.

In a preferred embodiment, the distillation step or steps are carried out in the presence of an additive, such as polyethylenglycol (PEG), for example PEG-300.

In a preferred embodiment, the reaction product is obtained at a yield of at least 98%, preferably at least 98.5% or at least 99%, and/or at an enantiomeric purity of at least 92% (e.e.), preferably at least 95% or at least 96% (e.e.) in the inventive hydrogenation reaction. As known in the art, the yield and enantiomeric yield can be reduced in the subsequent distillation at increased temperatures. However, it was found that even after the separation of the product from the reaction mixture, a total yield above 80% and an enantiomeric yield above 92%, preferably above 95% (e.e.) was obtained. The purity of the product was above 93%.

The enantiomeric excess (e.e.) is defined as the absolute difference between the mole fractions of each enantiomer in percent. As an example, a sample with 90% of S-isomer and 10% of R-isomer has an enantiomeric excess of 80% S-isomer.

Subject of the invention is also a process for the production of L-carnitine, comprising converting ethyl-4-chloroacetoacetate to (R)-ethyl-4-chloro-3-hydroxybutyrate in a process of the invention and subsequent conversion of (R)-ethyl-4-chloro-3-hydroxybutyrate to L-carnitine. Preferably, the subsequent conversion to L-carnitine is carried out by amination and hydrolysis, preferably in the presence of tertiary amine and a metal hydroxide base, more preferably in the presence of trimethylamine and sodium hydroxide. This process step is known in the art, for example from EP 0 339 764 A1. In another embodiment of the invention, the process for producing L-carnitine comprises an initial step, in which the β-ketoester is produced by hydrolysis and ring opening of a diketene, preferably by halogenation, especially chlorination of the diketene.

The reaction product can be converted to L-carnitine by subsequent amination and hydrolysis after isolation of the reaction product, or in the same reactor. The L-carnitine product may be purified further by crystallization, pervaporation, nanofiltration, membrane separation, membrane filtration, electrodialysis, diafiltration, reverse osmosis, liquid chromatography (LC), HPLC, extraction, ion exchange chromatography and the like.

Another subject of the invention is thus the use of a process of the invention in a method for the production of L-carnitine.

The inventive process solves the above mentioned problems. A highly pure (S)- or (R)-4-halo-3-hydroxybutyrate is obtainable by the inventive process. The inventive process is applicable in a simple manner with a low number of process steps. The process provides the (S)- or (R)-4-halo-3-hydroxybutyrate at high enantiomeric purity and also at high yield. The process is less cost- and labour-intensive compared to processes known in the art.

Specifically, the process can be carried out with only low amounts of catalyst and without additional additives, such as additional acids or bases. The amount of solvent necessary is relatively low, which results in a significant decrease of the overall consumption of chemicals with a high throughput at the same time. Even further, due to the high purity of the product, the solvent can be reused and thus the solvent consumption is further decreased. Specific solvent mixtures are disclosed which enhance the efficiency. The inventive process can be carried out in a simple batch process.

The process is also energy efficient, because although only low amounts of catalyst are used, the reaction time is low. Further, the pressure can be maintained relatively low, which is advantageous in an industrial large scale process for economic and safety reasons.

The specific inventive combination of catalysts with substrates and process conditions is not known from the prior art. For example, EP 0 295 109 discloses the use of ruthenium catalysts, which do not comprise an aromatic group Ar as in the present invention. EP 0 366 390 discloses a large number of catalysts, comprising some as in the present invention. However, when reacting methyl acetoacetate with [RuCl(p-cymene)((S)-BINAP)]Cl, a substrate/catalyst ratio of 500 was necessary to obtain low total and optical yields below 90% (use example 3). Pavlov et al. (Russ. Chem. Bull., 2000, 49, p728-731) study a specific combination of a β-ketoester with BINAP ruthenium catalysts according to the present invention, but require relatively high amounts of solvent and catalyst (tables 1 and 2, FIG. 1) and high pressure, whereas the enantiomeric yields are often not sufficient.

In summary, the present invention provides a novel, simple and efficient process for the production of (S)- or (R)-4-halo-3-hydroxybutyrate.

BRIEF DESCRIPTION OF THE DRAWINGS

FIG. 2 comprises table 1, which summarizes conditions and results of working examples 3 to 17.

FIG. 3 comprises table 2, which summarizes conditions and results of working examples 18 to 22 and table 3, which summarizes conditions and results of working examples 23 to 27.

FIG. 4 shows the structure of ligands a) SEGPHOS, b) Cn-TunePhos, c) P-Phos, d) MeO-BIPHEP, e) tetraMe-BI-TIOP and f) BINAP.

WORKING EXAMPLES

Example 1

Synthesis of (R)-ethyl-4-chlorohydroxybutyrate (HBusEt)

1. Batch Process Hydrogenation

Figure 1:
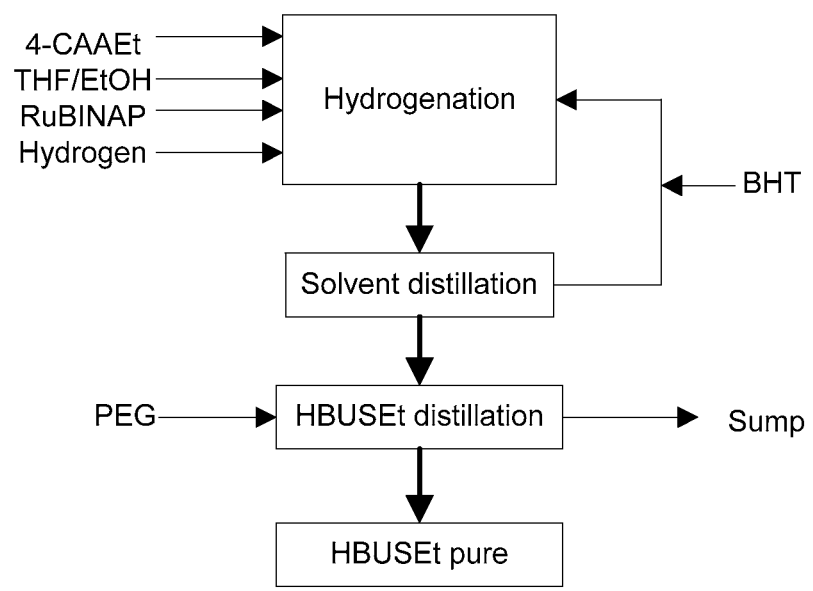
FIG. 1 provides a flowchart of an exemplified inventive process with a BINAP catalyst.
The following abbreviations are used:
4-CAAEt: ethyl-4-chloroacetoacetate
THF: tetrahydrofurane
RuBINAP: (S)-(−)-BINAP-Cl(cymene)RuCl
BHT: butylhydroxytoluene
PEG: polyethylenglycol
HBUSEt: (S)-ethyl-4-chloro-3-hydroxybutyrate
The sump comprises the bottom product.

In an inert atmosphere, 100 g ethyl-4-chloroaetoacetate (CAAEt), 50 g ethanol, 50 g THF and 8.1 mg (S)-(−)-BINAP-Cl (cymene)RuCl (purchased from Takasago, Japan) are filled in an autoclave. The solution is heated to 100° C., pressurized to 15 bar with hydrogen and stirred for 3 to 4.5 hours. The conversion was 99% and 95.5% ee. Removal of the solvents by distillation and subsequent distillation of the residue lead to (R)-HBusEt in 95-97% yield (>93% purity, 95.5% ee).
Reaction Parameters:
Ethanol (absolute): technical grade
Tetrahydrofuran (THF): technical grade stabilized with BHT (anti-peroxides)
In the following batches, recycled solvents were used. BHT was added to stabilize the THF and to avoid peroxide formation.
4-CAAEt: 90.6-97%, technical grade
Hydrogen: Quality 5.0 due to oxygen content
T: 100° C.
p(H2): 15 bar
Molar ratio Substrate/Catalyst (S/C): 70,000
Solvent: EtOH/THF 1:1 (wt-%)
[S]: 50 wt %
Reaction time: 3.2-4.4 h
Conversion: 99%

Example 2

Distillation 2.1 Batch

The distillation was carried out in a batch mode by adding PEG-300 (25-50 wt. % with respect to HBuSEt) to the crude reaction mixture. In a first step, the low boilers, mainly EtOH and THF with traces of chloroacetone, were distilled off using a vacuum of 200 mbar while slowly warming up from 48° C. to 60° C. A middle fraction was isolated from 60-100° C. at 200 mbar. Finally the high boilers (HBusEt) were distilled at 1-5 mbar and 100-130° C.
Results:
Yield (reaction plus distillation): 83.8-85.8 Purity>95%
ee (reaction+distillation): 95.5%

2.2 Continuous:

The solvent was recycled in a continuous distillation. A column with a diameter of 28 mm was used. The following parameters were used:
Feed: 200 g/h
Feed location: in the middle of the column
R/D: 4:1
P: 80 mbar
Head T: 19-21° C.
Sump T: 98-103° C.

The composition of the distillate was determined by gas chromatography and the missing amounts of THF and EtOH adjusted with fresh material.

(R)-HBusEt was isolated by distillation with the following parameters:
Feed: 300 g/h
Head T: 99-102° C.
Jacket T: 148° C.
PEG-300:1% w/w
Pressure: 7-8 mbar
Results:
Yield (reaction plus distillation): 95-96
Purity: >93%
ee (reaction+distillation): 95.5%

Examples 3 to 17

The reaction of example 1 was carried out with different catalysts and under varying conditions. The specific catalysts, conditions and results are summarized in table 1 in FIG. 2. Unless specified otherwise in FIG. 2, the reaction was carried out as described above for example 1. The solvent used in all reactions was EtOH/THF. The ratio substrate/catalyst (S/C) was relatively high in most experiments. Thus only low amounts of catalyst are necessary in the inventive reaction. Further, the concentration of the substrate S was selected relatively high to 3 or 4 M. This is equivalent to a concentration of approximately 50% (w/w). The temperature was 100° C. The pressures were adjusted to relatively low levels of between 15 and 40 bar.

The results show, that for almost all catalysts a high absolute yield (conversion) and a high enantiomeric yield (ee) were obtained, although the total amounts of catalyst were very low. Further, the pressure was relatively low, which is advantageous for large scale industrial applications. High yields could be obtained even after relatively short reaction times of between 1.3 and 3 hours (examples 8 to 13). Overall, the examples show that the inventive reaction is efficient and can be carried out with low amounts of catalyst and solvent. The reaction is also energy-efficient, because the reaction time is low, the volume to be heated is small (due to low solvent levels) and the pressure is low.

Examples 18 to 22

The reaction was carried out with (S)-(−) BINAP Cl(cymene)RuCl in the presence of different solvents. The solvents, conditions and results are summarized in table 2 in FIG. 3. Examples 18, 21 and 22 are comparative. Unless specified otherwise in table 2, the reaction was carried out as described above for example 1. The results show, that the highest enantiomeric yields are obtained with EtOH/THF and EtOH/acetone, although the reaction times are significantly shorter.

Examples 23 to 27

The reaction was carried out under the specific conditions as summarized in table 3 of FIG. 3. Unless specified otherwise in table 2, the reaction was carried out as described above for example 1. Reactions were carried out at a relatively low temperature of 60° C. (ex. 23, 25, 27) or relatively low pressure (ex. 24, 26). The results show that the reaction may be relatively slow at 60° C. When using higher amounts of catalyst, the reaction may also be efficient at 60° C. (ex. 27). At 15 bar, some reactions may be slightly slower compared to higher pressure and may require higher reaction times.

The invention claimed is:

1. A process for the production of an (S)- or (R)-4-halo-3-hydroxybutyrate, comprising reacting a 4-haloacetoacetate with hydrogen in the presence of a solvent, the solvent being a solvent mixture, which comprises a first solvent and a second solvent, wherein the first solvent is an aliphatic alcohol and the second solvent is aprotic and comprises at least one oxygen atom; and a catalyst of the formula [RuXYZ]X, wherein
   X is halogen, OAc, acetoacetate, allyl or $ClO_4$,
   Y is a bidentate organic ligand having two phosphine groups, and
   Z is an arene, a polyene, or an alkene.

2. The process of claim 1, wherein Y has the formula $X_2P—Z—PX_2$, wherein Z comprises at least one aromatic hydrocarbon, the residues X are selected independently from each other, and at least one residue X is an aryl or araryl group.

3. The process of claim 1, wherein Y has the formula (I)

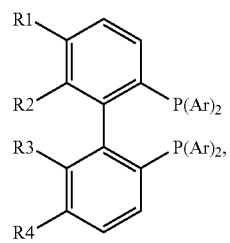

wherein
   Ar are aryl or araryl groups, wherein Ar are selected independently from each other, and R1, R2, R3 and R4 are selected independently from each other, and are selected from H, OH, halogen and organic side chains having 1 to 10 C-atoms, or wherein Y is a derivative of a compound of formula (I), in which at least one phenyl ring, preferably both biphenyl rings, is/are substituted each by heterocyclic aromatic rings, wherein the residues R1, R2, R3 and R4 are at positions of the aromatic rings, which are different from those in formula (I), preferably at the α-positions next to the heteroatoms.

4. The process of claim 1, wherein Y is selected from BINAP, SEGPHOS, TunePhos, P-Phos, BITIOP, BIPHEP, and derivatives thereof.

5. The process of claim 1, wherein the catalyst is selected from [RuCl(p-cymene)((S)-BINAP)]Cl, [(R)Xyl-P-Phos-Ru(benzene)Cl]Cl, [(R)P-Phos-Ru(benzene)Cl]Cl, [(S)Xyl-P-Phos-Ru(benzene)Cl]Cl, [RuCl(p-cymeme)((S)-SEGPHOS)]Cl, (S)-(−) BINAP Cl(cymene)RuCl, (R)-tetra-Me-BITIOP[$RuCl_2$(p-cymol)]$_2$, [(S)-C3-TunePhosRu(p-cymene)Cl]Cl and [(R)-MeO-BIPHEP-Ru(c-cymene)Cl]Cl.

6. A process for the production of an (S)- or (R)-4-halo-3-hydroxybutyrate according to claim 1, comprising reacting a 4-haloacetoacetate with hydrogen in the presence of a solvent in the presence of a catalyst of the formula [RuXArY]X, wherein
   X is halogen, OAc, allyl or $ClO_4$,
   Y is BINAP, or a derivative of BINAP having at least one aromatic ring substituted with an alkyl group,
   Ar is an arene.

7. The process of claim 1, wherein the 4-haloacetoacetate is a methyl, ethyl, 1-propyl, 2-propyl, 1-butyl, 2-butyl or tert-butyl ester.

8. The process of claim 1, wherein the second solvent is an ether a ketone, or an ester.

9. The process of claim 1, wherein the first solvent is methanol, ethanol, 1-propanol, 2-propanol, 1-butanol, 2-butanol or tert-butanol, and the second solvent is tetrahydrofuran.

10. The process of claim 1, wherein the ratio of the first solvent to the second solvent is between 5:1 and 1:5 (w/w).

11. The process of claim 1, wherein the concentration of the 4-haloacetoacetate in the solvent mixture is at least 25% (v/v).

12. The process of claim 1, wherein the molar ratio 4-haloacetoacetate/catalyst is above 35,000.

13. The process of claim 1, wherein the process is a batch process.

14. The process of claim 1, wherein the reaction mixture does not comprise an additional acid or base.

15. The process of claim 1, wherein the solvent is separated from the reaction mixture by distillation and reused in the process.

16. The process of claim 1, wherein the 4-haloacetoacetate is ethyl-4-chloroacetoacetate and the product is (R)-ethyl-4-chloro-3-hydroxybutyrate.

17. The process of claim 1, wherein the catalyst is [RuCl(p-cymene)((S)-BINAP)]Cl.

18. The process of claim 1, wherein the reaction is carried out in the presence of hydrogen at a pressure between 5 bar and 200 bar and at a temperature between 70° C. and 130° C.

19. The process of claim 15, wherein after separating the solvent mixture from the reaction mixture by a first distillation, the 4-halo-3-hydroxybutyrate is separated by a second distillation.

20. The process of claim 1, wherein the 4-haloacetoacetate is obtained in a yield of at least 98% and at an enantiomeric purity of at least 92% ee.

21. A process for the production of L-carnitine, comprising converting ethyl-4-chloroacetoacetate to (R)-ethyl-4-chloro-3-hydroxybutyrate in a process of claim 1 and subsequent conversion of (R)-ethyl-4-chloro-3-hydroxybutyrate to L-carnitine.

22. The process of claim 16, wherein after separating the solvent mixture from the reaction mixture by a first distillation, the 4-halo-3-hydroxybutyrate is separated by a second distillation.

23. The process of claim 17, wherein after separating the solvent mixture from the reaction mixture by a first distillation, the 4-halo-3-hydroxybutyrate is separated by a second distillation.

24. The process of claim 18, wherein after separating the solvent mixture from the reaction mixture by a first distillation, the 4-halo-3-hydroxybutyrate is separated by a second distillation.

25. The process of claim 1 wherein X is halogen and is selected from Cl or Br, and Z is an arene selected from cymene, benzene, xylene or toluene, or Z is a diene.

26. The process of claim 3 wherein Ar is phenyl or phenyl substituted with alkyl side chains having 1 to 10 carbon atoms and R1, R2, R3, and R4 are organic side chains having 1 to 10 C-atoms, selected from alkyl, alkoxy, or cyclic alkoxy groups bridging residue R1 with R2, or residue R3 with R4, or residue R2 with R3.

27. The process of claim 6 wherein X is Cl, and Ar is an arene selected from cymene, benzene, xylene or toluene.

28. The process of claim 8 wherein the second solvent is tetrahydrofuran, acetone, or ethylacetate.

29. The process of claim 18, wherein the reaction is carried out in the presence of hydrogen at a pressure between 5 bar and 40 bar.

* * * * *